United States Patent [19]

Kirk et al.

[11] Patent Number: 4,860,740
[45] Date of Patent: Aug. 29, 1989

[54] POWDER INHALATION DEVICE

[75] Inventors: William F. Kirk, Loughborough; Anthony C. L. Wass, Duddington; Eric A. Baum, Bishops Stortford; Ian P. Tansey, Barrow on Soare Loughborough; William G. Meredith, Rothley, all of United Kingdom

[73] Assignee: Riker Laboratories, Inc., St. Paul, Minn.

[21] Appl. No.: 13,191

[22] Filed: Feb. 10, 1987

Related U.S. Application Data

[63] Continuation of Ser. No. 679,602, Dec. 7, 1984, abandoned, which is a continuation of Ser. No. 403,768, Jun. 29, 1982, abandoned.

[30] Foreign Application Priority Data

Oct. 30, 1980 [GB] United Kingdom ............ 8034867

[51] Int. Cl.$^4$ ............................................. A61M 15/00
[52] U.S. Cl. .................................. 128/203.15; 664/58; 222/144; 222/145
[58] Field of Search ................. 128/203.15, 203.21, 128/203.23; 604/57, 58; 222/636, 637, 4, 144, 145, 169, 636

[56] References Cited

U.S. PATENT DOCUMENTS

| | | |
|---|---|---|
| 2,587,215 | 2/1952 | Priestly ............................ 128/203.15 |
| 3,518,992 | 7/1970 | Altounyan et al. . |
| 3,795,244 | 3/1974 | Lax et al. . |
| 3,858,583 | 1/1975 | Hallworth et al. . |
| 3,870,046 | 3/1975 | Elliott ............................ 126/203.15 |
| 3,888,253 | 6/1975 | Watt et al. . |
| 3,918,451 | 11/1975 | Steil . |
| 3,964,483 | 6/1976 | Mathes . |
| 3,973,566 | 8/1976 | Mathes . |
| 3,991,761 | 11/1976 | Cocozza . |
| 4,005,711 | 2/1977 | Glenn . |
| 4,013,075 | 3/1977 | Cocozza . |
| 4,014,336 | 3/1977 | Mathes . |
| 4,064,878 | 12/1977 | Lundquist . |
| 4,069,819 | 1/1978 | Valentini . |
| 4,116,195 | 9/1978 | James ............................ 128/203.15 |
| 4,117,844 | 10/1978 | James ............................ 128/203.15 |
| 4,206,758 | 6/1980 | Hallworth et al. ............ 128/203.15 |
| 4,210,140 | 7/1980 | James et al. .................... 128/203.15 |
| 4,240,418 | 12/1980 | Rossamp et al. ............... 128/203.15 |
| 4,446,862 | 5/1984 | Baum et al. . |

FOREIGN PATENT DOCUMENTS

| | | |
|---|---|---|
| 1118341 | 7/1968 | United Kingdom . |
| 1331216 | 9/1973 | United Kingdom . |
| 2061735 | 5/1981 | United Kingdom ........... 128/203.15 |
| 2064334 | 6/1981 | United Kingdom ........... 128/203.15 |

Primary Examiner—Max Hindenburg
Assistant Examiner—K. M. Reichle
Attorney, Agent, or Firm—Donald M. Sell; Walter N. Kirn; Stephen W. Bauer

[57] ABSTRACT

A device facilitating the inhalation of powdered medicaments from within a container. The device comprises a body having walls partially defining a chamber, an inlet port into the chamber for the entry of air, and a mouthpiece having a central through opening communicating with the chamber. A support member also partially defines the chamber and is manually movable relative to the body to convey a first portion of the container from (1) a first position spaced from the chamber to (2) a predetermined dispense position within the chamber with an open end of the first capsule portion uppermost so that airflow into the inlet port and through the chamber induced by suction at the mouthpiece will cause the powdered medicament in the first container portion to become entrained in the airflow; and an extractor is mounted for movement relative to the body to remove a second container portion and open the container prior to positioning of the first container portion at the dispense position.

7 Claims, 3 Drawing Sheets

POWDER INHALATION DEVICE

This application is a continuation of application Ser. No. 679,602, filed Dec. 12, 1984, now abandoned, (which is a continuation of application Ser. No. 403,768, filed June 29, 1982, now abandoned).

TECHNICAL FIELD

This invention relates to devices which facilitate the inhalation of powdered medicaments.

BACKGROUND ART

There are many devices which facilitate the inhalation of powdered medicaments by the use of propellants, such as compressed or liquified gases, to dispense and disperse the medicament. These devices may be complex to construct and have the disadvantage that in order for the optimum effect to be obtained it is essential that inhalation and dispensing be synchronous.

There are also a number of known breath-actuated inhalation devices for administering powdered medicaments to the lungs. The powdered medicament is typically supplied in commercially available capsules which comprise first and second capsule portions, each including a tubular part having an open end and an end wall opposite its open end, with the open end and tubular part of one portion being received through the open end of the other of the tubular parts in mechanical or frictional engagement to retain the powdered medicament therein. In the simpler breath-actuated devices the capsule is opened prior to insertion into the device and one capsule portion containing the medicament or the medicament itself is positioned in the device such that during inhalation through the mouthpiece the medicament becomes entrained in the air stream and passes to the patient. Examples of such devices are disclosed in British Patent Specification Nos. 1,520,064; 1,504,441; 1,118,341; 1,520,063 and 1,520,062. These devices suffer from the disadvantage that medicament may be spilled when the capsule is opened prior to insertion in the device.

British Patent Specifications Nos. 1,521,000; 1,520,062; 1,472,650 and 1,502,150 disclose more complex devices in which the complete capsule is inserted into the device, thus ensuring no spillage of medicament prior to inhalation, and access to the medicament is gained by piercing the capsule or cutting it in half inside the dispensing device. On inhalation the air flows into or through the capsule and the powder within is entrained in the air stream and carried towards the mouth.

The devices disclosed in British Patent Specifications Nos. 1,485,163; 1,331,216; 1,457,352; 1,396,258; 1,182,779; 1,404,338; 1,459,426 and 1,118,341 and U.S. Pat. Nos. 4,117,844 and 4,116,195 are designed to agitate the capsule containing the medicament in order to help release and disperse the powder from the capsule. The capsule may be agitated by various means, including creating a turbulent air flow, or by rotating and/or vibrating the capsule through the use of vanes or propellers. These devices are complex and are often difficult to operate.

U.S. Pat. No. 4,210,140 discloses a device in which access to the powdered medicament is gained by pulling the capsule portions apart so that the medicament is emptied to a suitable position for entrainment in the air flow caused by inhalation.

Our copending PCT Publication No. 81/01243 discloses breath-actuated devices for the oral inhalation of powdered medicaments. Those devices each comprise a chamber having at least one inlet port for the entry of air and in direct communication with a mouthpiece; means within the chamber for holding a capsule containing a medicament substantially vertically; and means for separating the capsule portions within the chamber to expose the open end of the lowermost capsule portion and afford access to the powdered medicament within in a position such that when the device is operated by suction at the mouthpiece, air flows essentially transversely across the open end of the lowermost capsule portion, causing the particles of powdered medicament therein to become entrained in the air.

The devices described in that application are easy and simple to use, reduce the possibility of the user spilling the medicament and ensure that any medicament that is spilled will still be inhaled, and are very efficient when compared to breath-actuated devices of the prior art. Positioning the means for separating the capsule portions in the chamber, however, presents possibilities for air leaks into the chamber, and restricts the design possibilities to provide a desired air flow pattern through the chamber.

DISCLOSURE OF INVENTION

The present invention provides a breath-actuated device which facilitates the inhalation of powdered medicaments from within a container such as a capsule, which device both includes a mechanism to assist the user in separating portions of the container and allows the device to provide an optimum air flow pattern through a chamber in which the separated container portion is positioned to afford dispersion of the powder.

According to the present invention there is provided a device facilitating the inhalation of powdered medicaments from within a container comprising a first container portion adapted to contain the powder and having an open end, and a second container portion closing the open end in the first container portion. The device comprises a body having walls defining a chamber, at least one inlet port into the chamber for the entry of air, and a mouthpiece having a central through opening communicating with the chamber. A manually-activatable means mounted on the body is provided for conveying the first container portion from a first position spaced from the chamber to a predetermined dispense position within the chamber with the open end of the first container portion uppermost so that airflow into the inlet port and through the chamber induced by suction at the mouthpiece will cause the powdered medicament in the first container portion to become entrained in the airflow. Also provided is a manually-activatable means mounted on the body for removing the second container portion from the first container portion prior to positioning of the first container portion at the dispense position by the means for conveying (i.e., prior to or during movement of the first container portion to the dispense position).

Devices according to the present invention can be adapted to receive containers in the form of conventional capsules used in the pharmaceutical industry which, as described above, comprise first and second capsule portions each including a tubular part having an open end and an end wall opposite its open end, with the open end and tubular part of one portion being received through the open end of the other and the tubular parts in frictional or mechanical engagement to retain the powdered medicament therein. Alternatively, however, devices according to the present invention can be adapted for use with containers of other shapes in which access to powder in a first container portion is gained by displacing a second container portion from an opening of the first container portion (e.g., by displacing a second container portion in the form of a bung or an adhered or crimped foil lid from an open end of a first container portion of any suitable shape); or which may have the first container portion integrally formed in a movable portion thereof providing the means for conveying, with a wall of the body of the device providing the second container portion or with the second container portion being provided by a foil lid over the open end of the first container portion.

The means for conveying the first portion of the container in a device according to the present invention can comprise a generally cylindrical support member rotatably mounted on the body of the device which is adapted to convey a number of first container portions seriatim from the first to the dispense position. Where such a device is adapted for use with conventional capsules of the type described above, the support member may have a plurality of radially-extending sockets opening through its periphery with each of the sockets being adapted to receive and hold the first portion of one of the capsules with the second portion of the capsule projecting radially outwardly of the support member. The means for removing the second capsule portion may comprise an extractor having at least one gripping wall with a surface adapted to engage the second capsule portion, which extractor is mounted on the housing for movement between a raised position with the gripping wall spaced from a capsule in the support member at the first position, and an engage position with the gripping wall in engagement with the second portion of a capsule in the support member at the first position.

Further, the device may include coupling means engageable between the support member and the extractor for moving the support member to convey an opened first capsule portion from the first position to the dispense position during movement of the extractor from its engage to its raised position. This coupling means can be a ratchet assembly comprising a wheel having teeth about its periphery coaxially attached to the support member, and a pawl coupled to the extractor and adapted to engage and advance the wheel upon movement of the extractor from its engage to its raised position.

The extractor can be a separate member movably mounted on the body, or can be incorporated in a cover for the device pivotably mounted on the body and having a portion positioned over the opening in the mouthpiece to close the opening when the extractor is in its engage position; but which portion is positioned away from the mouthpiece when the extractor is in its raised position.

The inlet port and chamber can be arranged to provide an airflow which is directed generally transversely across the open end of the first container portion and not substantially into the first container portion. This airflow pattern is effective in entraining powder from the container possibly due to a resonance effect produced in the container in a manner similar to the resonance produced by blowing over the top of an open bottle. Tests which have been conducted reveal that for airflow patterns generally transversely across the open end of the first portion of a capsule there tends to be an optimum position for the open end of the first capsule portion relative to the surface defining the lower side of the inlet port. This optimum position may vary according to the capsule portion dimensions and the amount of medicament in the capsule portion. It does not tend to be critical for capsule portions which are relatively shallow, (e.g., up to 10 mm), but becomes more critical when deeper capsule portions are used. In general it has been found that the open end of the capsule should not extend significantly above the surface defining the lower side of the inlet port and is preferably at the same level or slightly lower than the surface defining the lower side of the inlet port so that the medicament in the capsule portion is spaced slightly below the mainstream of the airflow. PCT Publication No. 81/01243, incorporated herein by reference, discloses further details of the relative positions of air inlets, capsule portion and mouthpieces together with experimental results.

The device according to the present invention can also be designed so that a portion or all of the airflow through the chamber enters the first container portion to scour the powdered medicament therefrom. In one embodiment which uses capsules and incorporates that feature an upper surface of the chamber slopes downwardly upstream of the dispense position for the first capsule portion and slopes upwardly downstream of the dispense position with the intersection of the sloping upper surfaces generally aligned with the longitudinal axis of the first capsule portion at the dispense position and closely spaced from the open end of that first capsule portion. In another such embodiment, the inlet port is positioned above the dispense position to direct substantially all of the airflow through the chamber axially into the open end of the first capsule portion and then through the mouthpiece.

The chamber should be designed so that the velocity of the air into or across the open end of the container portion is high. However, the pressure drop across the chamber in use should not be high since this would require the user to exert considerable suction at a time when he is in a distressed condition. With the present invention it is possible to achieve an adequate airflow velocity into or across the first container portion and yet cause a pressure drop across the chamber which is barely noticeable to the user. A pressure drop of up to 50 cm of water appears to be an upper limit as far as comfort to the user is concerned.

The mouthpiece is preferably short and straight and can be aligned with airflow transversely across the open end of the first container portion so that there is substantially straight airflow through the device. However, the mouthpiece may be shaped or inclined with respect to airflow across the first container portion without significantly affecting the efficiency of the device providing there are no obstructions which will trap the particles entrained in the airflow. It may be advantageous for the cross-sectional area of the mouthpiece to increase suddenly so that any large or agglomerated particles in the powdered medicament will settle in the mouthpiece rather than deposit into the patient's mouth or nasal passages. The mouthpiece of the device may be adapted for nasal inhalation and the term "mouthpiece" as used herein includes such nasal adaptors.

BRIEF DESCRIPTION OF DRAWING

The invention will be further described with reference to the accompanying drawings wherein like numbers refer to like parts in the several views, and wherein.

DETAILED DESCRIPTION

Referring now to FIGS. 1, 2 and 3a through 3f, there is illustrated a first embodiment of a device according to the present invention, generally designated by the reference numeral 10.

Figure 3B:
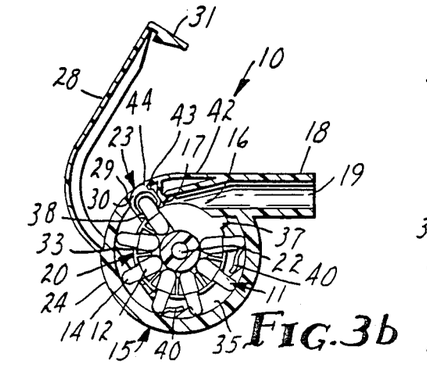
Figure 3C:
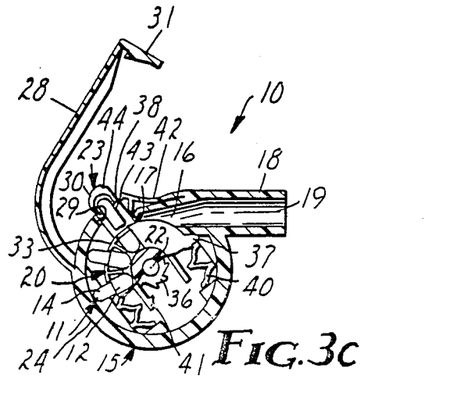
Figure 3D:
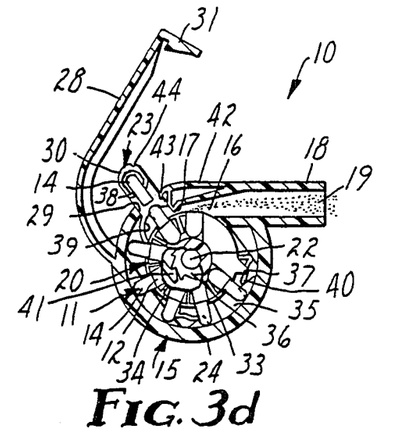
Figure 3E:
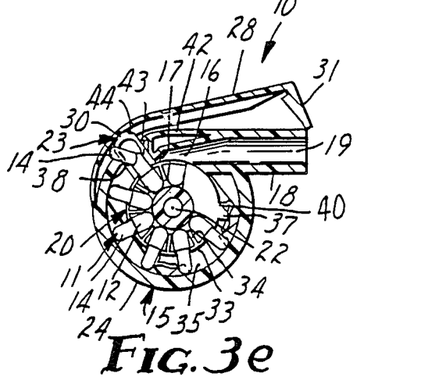

The device 10 is adapted to facilitate oral inhalation of powdered medicaments from within a container in the form of a capsule 11 of the commercially available type comprising first and second container or capsule portions 12 and 14, each of which capsule portions 12 and 14 includes a cylindrically tubular part having an open end and a hemispherical end wall opposite its open end, with the open end and tubular part of one capsule portion being received through the open end of the other and the tubular parts being in engagement to retain the powdered medicament therein. Generally the device comprises a body 15 having walls partially defining a chamber 16 free of obstructions, at least one air inlet port 17 into the chamber 16, and a mouthpiece 18 having a central through opening 19 communicating directly with the chamber 16. Manually-activatable means in the form of a generally cylindrical capsule support member 20 is mounted on the body 15 for rotation about a post 22 to convey the first capsule portion 12 from a first position (FIG. 3c) spaced from the chamber 16 to a predetermined dispense position (FIG. 3d) within the chamber 16 (which chamber 16 is partially defined by the periphery of the support member 20). In the dispense position the support member 20 positions the open end of the first capsule portion 12 uppermost so that airflow into the inlet port 17 and through the chamber 16 induced by suction through the mouthpiece 18 will flow substantially transversely across the open end and cause the powdered medicament in the first capsule portion 12 to become entrained in the airflow. Manually-activatable means in the form of an extractor 23 slidably mounted on the body 15 is provided for removing the second capsule portion 14 prior to positioning of the first capsule portion 12 at the dispense position by movement of the support member 20 (FIGS. 3b and 3c).

The body 15, which is preferably injection molded of a suitable polymeric material, comprises a main portion 24 having walls, including a circular side wall from which the post 22 projects, which walls define a generally cylindrical cavity in which the capsule support member 20 and extractor 23 are mounted; and a side portion 25 hinged to the main portion 24 via a flexible hinge portion 26 which comprises a circular side wall from which centrally projects a cylindrical tube 27. The inner surface of the tube 27 is adapted to frictionally engage around the post 22 to retain the capsule support member 20 and extractor 23 within the cavity, and retain together the main and side portions 24 and 25 of the body 15. Also included in the body 15 is a cover 28 mounted at one end via a thin portion of the body 15 for pivotal movement between an open position spaced from the end of the mouth-piece 18 and an opening 29 in an edge wall of the body 15 through which an end portion 30 of the extractor 23 is received and guided (FIGS. 1, 3b, 3c and 3d); and a closed position (FIG. 3a) with a part of the cover 28 extending across the opening 29 and a distal hook-like portion 31 of the cover 28 extending across the mouthpiece opening 19, at which closed position the cover 28 is releasably retained by engagement of the upper edge of the mouthpiece 18 in a notch in the hook-like portion 31.

Figure 3F:
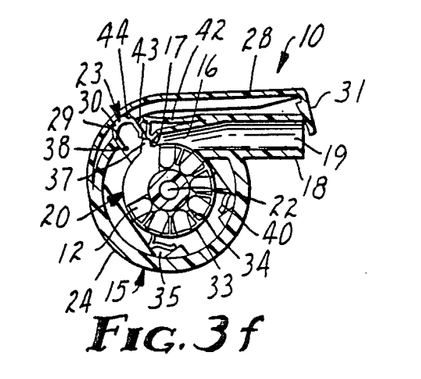

The capsule support member 20 comprises a circular side wall 32 with a central opening in which the post 22 is received; a cylindrical peripheral wall 33 with spaced orifices opening through the peripheral wall 33 through which orifices the smaller diameter second portions 14 of the capsules 11 may project; and radially-extending walls 34 projecting normally from the side wall 33 which together with parts of the peripheral wall 33 around the orifices define radially extending side entry sockets that receive and hold the larger diameter second portions 12 of the capsules 11 with their open ends at the orifices in the peripheral wall 33. Rotation of the support member 20 causes capsules 11 to move seriatim from an arcuate storage area 35 defined by portions of the body 15 and support member 20 to the first position as the first portion 12 of a preceding opened capsule 11 is moved to the dispense position. A projection 37 is formed on the support member 20. The projection 37 will move to the first position as the first portion 12 of the last unused capsule 11 in the device 10 moves to the dispense position and will interfere with operation of the extractor 23 and closing of the cover 28 to signal to a user that all the capsules 11 in the device 10 have been used (FIG. 3f). A toothed wheel 36 is coaxially formed on the side wall 32 opposite the walls 34 (FIG. 2); which toothed wheel 36 forms a part of a ratchet assembly that provides coupling means engageable between the support member 20 and the extractor 23 for moving the support member 20 to convey the first portion 12 of the capsule from the first position to the dispense position during movement of the extractor 23 after the extractor 23 has removed the second portion of capsule 11 as will be further explained hereinafter.

The extractor 23 comprises the end portion 30 guided by walls defining the opening 29 in the body 15. The end portion 30 includes an axially projecting arcuate wall-like part terminating in spaced gripping walls 38 having parallel edges spaced to frictionally engage the sides of the second portion 14 of a capsule 11. A generally U-shaped portion 39 of the extractor 23 projects from its end portion 30 and has opposed surfaces adapted to slide along and be guided by opposite surfaces of the toothed wheel 36. Such guidance of the extractor 23 allows it to slide radially with respect to the support member 20 between a raised position (FIG. 3d) with the gripping walls 38 spaced from a capsule 11 in the support member 20 at the first position, and an engage position (FIGS. 3a and 3b) with the gripping walls 38 in engagement with the second portion 14 of a capsule 11 at the first position. Two undulating, flexible, resilient spring portions 40 of the extractor 23 also project from the end portion 30 along opposite sides of the U-shaped portion 39 and provide spring means between the body 15 and extractor 23 for biasing the extractor 23 to its raised position. An inwardly projecting pawl 41 is positioned at the distal end of one leg of the U-shaped portion 39 and is adapted to engage the toothed wheel 36 to act as a pawl for the ratchet assembly and advance the capsule support member 20 so that a first capsule portion 12 is advanced from the first to the dispense position during a second part of movement of the extractor 23 from its engage to its raised position under the influence of the spring portions 40.

Latch means are provided for releasably latching the extractor 23 in its engage position. The body 15 includes a plate-like latch portion 42 which has one end attached at the wall defining the side of the opening 29 adjacent the mouthpiece 18 and its opposite end attached at the mouthpiece 18, with the center of the latch portion 42 normally being bowed upwardly away from the wall defining the upper surface of the chamber 16. The latch portion 42 includes a lip 43 which, when the latch portion 42 is bowed upwardly, projects into the opening 29 where it can engage a ledge 44 along the end portion 30 of the extractor 23 (FIG. 3b) and hold the extractor 23 in its engage position. The latch portion 42 may be manually pressed toward the wall defining the upper surface of the chamber 16 (FIG. 3c) which will cause the lip 43 to deflect away from the ledge 44 and allow the extractor 23 to move to its raised position.

Figures 1, 2, 3A:
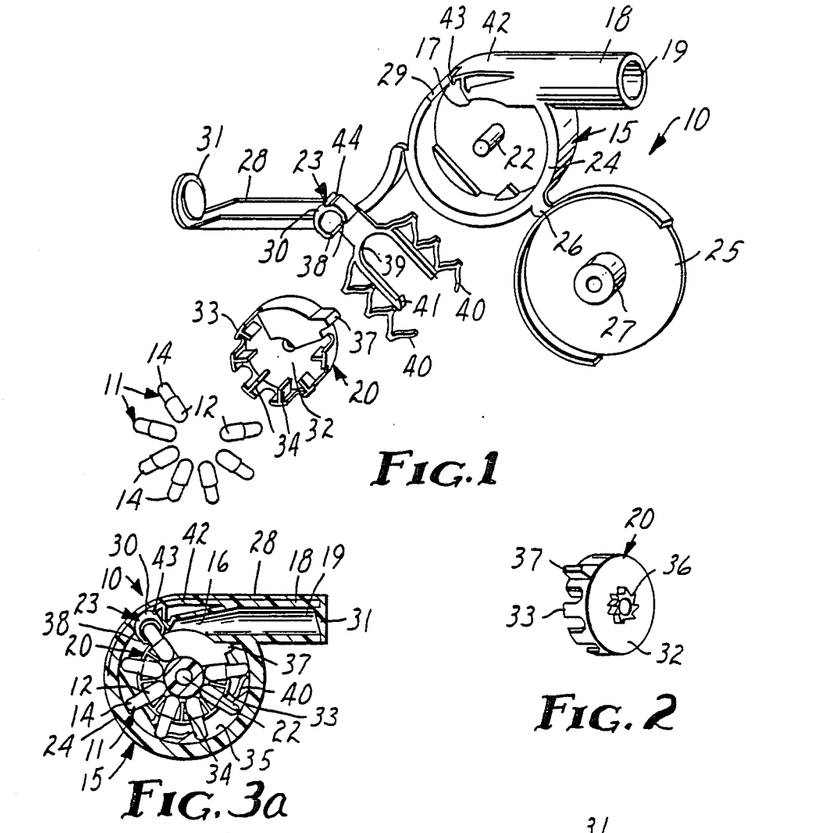
FIG. 1 is an exploded perspective view of a first embodiment of a device according to the present invention.
FIG. 2 is a perspective view of the back side of a capsule support member shown from its front side in FIG. 1.
FIGS. 3a through 3f are sectional views of the device of FIG. 1 illustrating its operating sequence and having parts broken away to show details.

The operation of the device 10 will now be explained assuming the extractor 23 is initially latched in its engage position via the latch means with the gripping walls 38 of the extractor 23 engaged with the second portion 14 of a capsule 11 at the first position, and the cover 28 is in its closed position (FIG. 3a). The user first opens the cover 28 by flexing the hook-like portion 31 of the cover 28 away from the mouthpiece 18 and pivots the cover 28 to its open position (FIG. 3b). Next, he releases the latch means by pressing the latch portion 42 toward the wall defining the top surface of the chamber 16, which moves the lip 43 away from the ledge 44 so that the extractor 23 slides from its engaged toward its raised position under the influence of the spring portions 40. During the first part of such movement the capsule portions 14 and 12 are pulled apart via frictional engagement of the extractor 23 with the second capsule portion 14 (FIG. 3c): During a second part of such movement the pawl 41 on the extractor 23 engages the toothed wheel 36 to advance the first capsule portion 12 from the first to the dispense position. The user may then inhale through the mouthpiece 18 which causes air to enter the chamber 16 through the inlet port 17, flow transversely across the open end of the first capsule portion 12 at the dispense position to entrain powdered medicament into the air stream, and be drawn into the user's lungs. Subsequently the user may move the cover 28 to its closed position, whereupon engagement of the cover 28 with the projecting end portion 30 of the extractor 23 moves the extractor 23 toward its engaged position so that the second capsule portion 14 is pushed through the spaced parallel edges of the (which edges frictionally engaged it) by the second portion 14 of the new closed capsule 11 at the first position (FIG. 3e) and is deflected to the side of the extractor 23 out of and away from the device 10 by an adjacent inner surface of the arcuate wall-like part of the end portion 30, after which the spaced parallel edges of the gripping walls 38 frictionally engage that new second capsule portion 14. There is sufficient friction between the post 22 and the capsule support member 20 so that as the extractor 23 is thus moved toward its engage position the leg of its U-shaped portion 39 supporting the pawl 41 will be deflected outwardly by sliding contact between the pawl 41 and the curved outer surface of the next tooth on the toothed wheel 36 so that the pawl 41 will pass around that tooth on the toothed wheel 36 rather than turn the capsule support member 20 backwards. When the extractor 23 reaches its engaged position, the lip 43 engages the ledge 44 to again releasably retain the extractor 23 in that position. The hook-like end portion 31 of the cover 28 again releasably engages the end of the mouthpiece 18 to retain it closed and the device 10 is ready to be used again.

Figures 4, 5, 6:
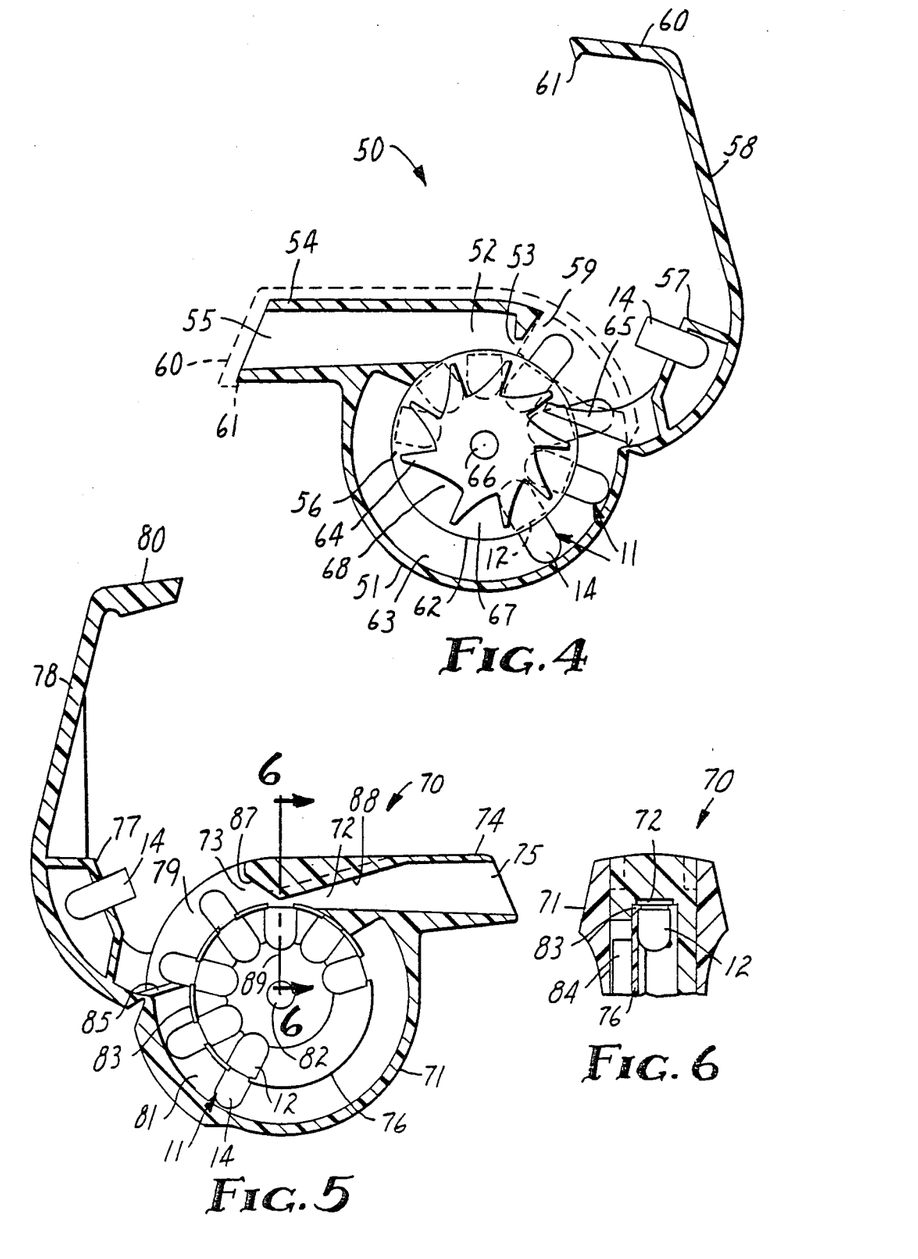
FIG. 4 is a sectional view of a second embodiment of a device according to the present invention.
FIG. 5 is a sectional view of a third embodiment of a device according to the present invention.
FIG. 6 is a fragmentary sectional view taken approximately along line 6—6 of FIG. 5.

Referring now to FIG. 4, there is illustrated a second embodiment of a device according to the present invention, generally designated by the reference numeral 50.

Like the device 10, the device 50 is adapted to facilitate oral inhalation of powdered medicaments from within a container in the form of a capsule 11 of the commercially available type described above comprising first and second container or capsule portions 12 and 14, and comprises a body 51 having walls partially defining an unobstructed chamber 52, at least one air inlet port 53 into the chamber 52 and a mouthpiece 54 having a central through opening 55 communicating directly with the chamber 52. Also, as in the device 10, manually-activatable means in the form of a generally cylindrical capsule support member 56 is rotatably mounted on the body 51 to convey the first capsule portion 12 from a first position spaced from the chamber 52 to a predetermined dispense position within the chamber 52 (which chamber 52 is partially defined by the periphery of the support member 56), and in the dispense position the support member 56 positions the open end of the first capsule portion 12 uppermost so that airflow through the inlet port 53 and the chamber 52 induced by suction through the mouthpiece 54 will flow substantially transversely across the open end and cause the powdered medicament in the first capsule portion 12 to become entrained in the airflow. Also, manually-activatable means is provided for removing the second capsule portion 14 prior to positioning of the first capsule portion 12 at the dispense position by movement of the support member 56, however unlike in the device 10, these means are provided by a wall or extractor 57 having a surface defining an opening and adapted to frictionally engage the second portion 14 of the capsule 11, which extractor 57 is incorporated into a cover 58 for the device 50.

The body 51 has walls defining a generally cylindrical cavity in which the capsule support member 56 is mounted for rotation about a post 66 included in the body 51. The cover 58 is integrally molded with the body 51 and is pivotably mounted at one end via a thin portion of the body 51 for pivotal movement between an open position spaced from the end of the mouthpiece 54 at which the extractor 57 is in a raised position spaced from an opening 59 in an edge wall of the body adjacent the first position; and a closed position at which the extractor 57 is in an engage position in the opening 59 and is engaged with the second portion 14 of a capsule 11 at the first position, and a hook-like distal portion 60 of the cover 58 extends across and closes the mouthpiece opening 55 and is releasably retained there by engagement of a lip 61 on the distal portion 60 with the lower edge of the mouthpiece 54.

The capsule support member 56 comprises a circular side wall 67 with a central opening in which the post 66 is received; a cylindrical peripheral wall 62 with spaced orifices opening through the peripheral wall 62 through which orifices the smaller diameter second portions 14 of the capsules 11 may project; and radially extending walls projecting normally from the side wall 67 which together with posts of the peripheral wall 62 around the orifices define radially extending side entry sockets that receive and hold the larger diameter second portions 12 of the capsules 11 with their open ends at the orifices. Rotation of the support member 56 causes capsule 11 to move seriatim from an arcuate storage area 63 defined by portions of the body 51 and support member 56, to the first position as a preceeding capsule 11 is opened and its first portion 12 is moved to the dispense position. A toothed wheel 64 is coaxially formed on one side of the support member 56, and with a pawl 65 fixed to and projecting from the cover 58 forms a ratchet assembly that provides coupling means engageable between the support member 56 and the extractor 57 for moving the support member 56 to convey the first portion 12 of the capsule from the first position to the dispense position during movement of the extractor 57 from its engage to its raised position (which occurs as the cover 58 is opened).

The operation of the device 50 will now be explained assuming that initially the cover 58 is closed so that the extractor 57 on the cover 58 is in its engage position and engaged with the second portion 14 of a capsule 11 at the first position. The user first opens the cover 58 by flexing the hook-like portion 60 of the cover 58 away from the mouthpiece 54 and pivots the cover 58 to its open position which moves the extractor 57 on the cover 58 from its engaged toward its raised position. During the first part of such movement the portions 14 and 12 of the capsule 11 at the first position are pulled apart via frictional engagement of the extractor 57 with the second capsule 14, and during a second part of such movement the pawl 65 on the cover 58 engages a tooth on the toothed wheel 64 to advance the open first capsule portion 12 from the first to the dispense position. The user may then inhale through the mouthpiece 54 which causes air to enter the chamber 52 through the inlet port 53, flow generally transversely across the open end of the first capsule portion 12 at the dispense position to entrain powdered medicament into the air stream, and be drawn into the user's lungs. Subsequently the user may remove the separated second capsule portion 14 from the extractor 57 and close the cover 58 so that extractor 57 engages the second portion 14 of the new capsule 11 at the first position. There is sufficient friction between the capsule support member 56 and the post 66 on which it is rotatably mounted so that as the cover 58 is closed the pawl 65 and the next tooth on the toothed wheel 64 deflect past each other because of the angular relationship of their surfaces that contact rather than causing the capsule support member 56 to turn backwards. When the extractor reaches its engaged position, the lip 61 engages the mouthpiece 54 to again releasably retain the cover 58 closed, and the device 50 is ready to be used again.

When the device 50 has been used a sufficient number of times that the first portion 12 of the last un-used capsule 11 in the support member 56 has been moved to the dispense position, a disproportionately wide space 68 between successive teeth on the toothed wheel 64 will be positioned adjacent the pawl 65 on the cover 58. The space 68 is sufficiently wide that upon subsequent closing of the cover 58 the pawl 65 will not contact and deflect by the next tooth on the toothed wheel 64. The freedom of cover movement thus produced will signal the user that the device 50 is empty.

Referring now to FIGS. 5 and 6, there is illustrated a third embodiment of a device according to the present invention, generally designated by the reference numeral 70.

Like the devices 10 and 50, the device 70 is adapted to facilitate oral inhalation of powdered medicaments from within a container in the form of a capsule 11 of the commercially available type described above comprising first and second container or capsule portions 12 and 14; and comprises a body 71 having walls partially defining a chamber 72, at least one air inlet port 73 into the chamber 72 and a mouthpiece 74 having a central through opening 75 communicating directly with the chamber 72. Also, as in the device 10 and 50, manually-activatable means in the form of a generally cylindrical capsule support member 76 is rotatably mounted on the body 71 to convey the first portion 12 of the capsule 11 from a first position spaced away from the chamber 72 to a predetermined dispense position within the chamber 72 (which chamber 72 is partially defined by the periphery of the support member 76), and in the dispense position the support member 76 positions the open end of the first capsule portion 12 uppermost so that airflow into the inlet port 73 and through the chamber 72 induced by suction through the mouthpiece 74 will cause the powdered medicament in the first portion 12 to become entrained in the airflow. As in the device 50, manually-activatable means in the form of a wall or extractor 77 having a surface defining an opening and adapted to frictionally engage the second capsule portion 14 is incorporated into a cover 78 for the device 70 and removes the second capsule portion 14 prior to positioning of the first capsule portion 12 at the dispense position by the means for conveying.

The body 71 has walls defining a generally cylindrical cavity in which the capsule support member 76 is mounted for rotation about a post 82 included in the body 71. The cover 78 is integrally molded with the body 71 and is mounted thereon for pivotal movement between an open position spaced from the end of the mouthpiece 74 at which the extractor 77 is in a raised position spaced from an opening 79 in an edge wall of the body adjacent the first position; and a closed position at which the extractor 77 is in an engage position in the opening 79 and is frictionally engaged with the second portion 14 of a capsule 11 at the first position, and a hook-like distal portion 80 of the cover 78 extending across and closing the mouthpiece opening 75 and releasably retained there by engagement of the upper edge of the mouthpiece 74 in a notch in the hook-like cover portion 80.

The capsule support member 76 comprises a cylindrical peripheral wall 83 with spaced orifices through which the second portions 14 of capsules 11 can project that open into radially extending sockets in the support member 76 in which the first portions 12 of capsules 11 are held and retained in the same manner as they are held and retained in the support members 20 and 56 of the devices 10 and 50. Rotation of the support member 76 causes capsules 11 to move seriatim from an arcuate storage area 81 defined by portions of the body 71 and support member 76 to the first position as a preceeding capsule 11 is opened and its first portion 12 is moved to the dispense position. A toothed wheel 84 is coaxially formed on one side of the support member 76 and with a pawl 85 projecting from and fixed to the cover 78 forms a ratchet assembly that provides coupling means engageable between the support member 76 and the extractor 77 on the cover 78 for moving the support member 76 to convey the first portion 12 of the capsule from the first position to the dispense position during movement of the extractor 77 on the cover 78 from its engage to its raised position (which occurs as the cover 78 is opened).

The device 70 is operated by a user and operates in essentially the same manner described above with respect to the device 50 and only differs significantly from that device by the shape of an inner surface of the upper wall defining the chamber 72. In the device 70 that part 87 of inner surface from the air inlet port 73 to the dispense position slopes downwardly, whereas a part 88 of that inner surface from the dispense position toward the mouthpiece 54 slopes upwardly. A longitudinal axis 89 of the first capsule portion 12 at the dispense position is aligned with the intersection of the sloping surface parts 87 and 88, and that intersection is above and close to the open end of the first capsule portion 12 at the dispense position. This arrangement causes some of the air inhaled through the chamber 72 to flow into the first capsule portion 12 and scour the powdered medicament therefrom. As a non-limiting example, good results have been achieved when the angle between the surface part 87 and the axis 89 is about 55°, the angle between the surface part 88 and the axis 89 is about 75°, and the intersection of the surface parts 87 and 88 is located about 1 millimeter above the open end of the first capsule portion 12. In general, both of the angles described above should be less than 80 degrees.

Figure 7:
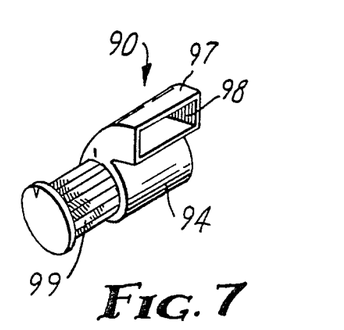
FIG. 7 is an exploded view of a fourth embodiment of a device according to the present invention.
Figure 8:
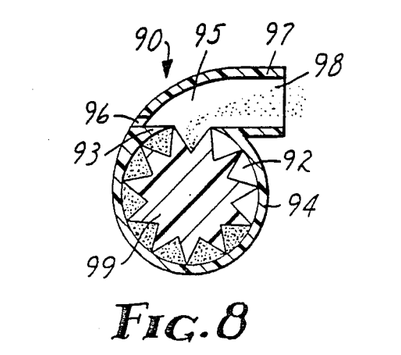
FIG. 8 is a sectional view of the device of FIG. 7.

Referring now to FIGS. 7 and 8, there is illustrated a fourth embodiment of a device according to the present invention, generally designated by the reference numeral 90.

Like the devices 10, 50 and 70, the device 90 is adapted to facilitate oral inhalation of powdered medicaments from within containers comprising first and second container portions 92 and 93; and comprises a body 94 having walls partially defining an unobstructed chamber 95, at least one air inlet port 96 into the chamber 95, and a mouthpiece 97 having a central through opening 98 communicating directly with the chamber 95. As in the devices 10, 50 and 70, manually-activatable means in the form of a generally cylindrical container support member 99 is rotatably mounted on the body 94 to convey the first container portion 92 from a first position spaced from the chamber 95 to a predetermined dispense position within the chamber 95 (which chamber 95 is partially defined by the periphery of the support member 99), and in the dispense position the support member 99 positions the open end of the first container portion 92 uppermost so that airflow into the inlet port 96 and through the chamber 95 induced by suction through the mouthpiece 97 will flow generally transverse of the open end of the first container portion 92 and cause the powdered medicament in the first container portion 92 to become entrained in the airflow. Also as in the devices 10, 50 and 70, manually-activated means is provided for removing the second container portion 93 prior to positioning of the first container portion 92 at the dispense position by the support member 99.

Unlike the devices 10, 50 and 70, however, the support member 99 of the device 90 has a plurality of the first container portions 92 integrally formed therein around its periphery, and the second container portion 93 is a wall on the body 94 that closes the first container portion 92 at the first position. Manual rotation of the support member 99 via a manually engageable knob at its end, thus causes the second container portion or wall 93 to be removed from over the first container portion 92 during movement of the first container portion 92 to the dispense position.

Figure 9:
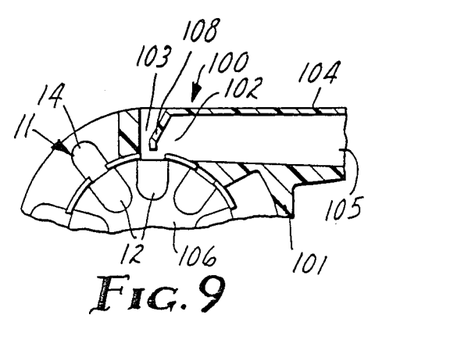
FIG. 9 is a fragmentary sectional view of a fifth embodiment of a device according to the present invention.

Referring now to FIG. 9, there is illustrated a fifth embodiment of a device according to the present invention, generally designated by the reference numeral 100.

Like the other illustrated devices, the device 100 is adapted to facilitate oral inhalation of powdered medicaments from within a container in the form of a capsule 11 comprising first and second container or capsule portions 12 and 14; and comprises a body 101 having walls partially defining a chamber 102, an air inlet port 103 into the chamber 102 and a mouthpiece 104 having a central through opening 105 communicating directly with the chamber 102. Also, manually-activatable means in the form of a generally cylindrical capsule support member 106 is rotatably mounted on the body 101 to convey the first portion 12 of the capsule 11 from a first position spaced away from the chamber 102 to a predetermined dispense position within the chamber 102 (which chamber 102 is partially defined by the periphery of the support member 106), and in the dispense position the support member 106 positions the open end of the first capsule portion 12 uppermost so that airflow into the inlet port 103 and through the chamber 102 induced by suction through the mouthpiece 104 will cause the powdered medicament in the first portion 12 to become entrained in the airflow. As in the devices 50 and 70, manually-activatable means (not shown) in the form of a wall or extractor having a surface defining an opening and adapted to frictionally engage the ,second capsule portion 14 is incorporated into a cover for the device and removes the second capsule portion 14 prior to positioning of the first capsule portion 12 at the dispense position by the means for conveying.

The operation and structure of the device 100 is essentially identical to the operation and structure of the devices 50 and 70 except for the shape of the inner surface of the upper wall defining the chamber 102 and the location of the inlet port 103. In the device 100, the inlet port 103 is positioned directly above the dispense position, and a part 108 of the upper wall of the chamber depends downwardly and is located essentially at the central axis of the second capsule portion 14 at the dispense position to direct substantially all of the airflow through the device 100 axially into one side of the first capsule portion 12 at the dispense position, and cause the airflow to change its direction of flow within the second capsule so that the powder is entrained in and flows with the air up out of the other side of the first capsule portion 12 and through the mouthpiece 104.

The devices 10, 50, 70, 90 or 100 may be made from any suitable polymeric material such as polypropylene or nylon, and at least portions of the devices may be sufficiently transparent that a user may readily determine when a first container portion is in the dispense position and how many unused containers remain in the device.

Having thus described the present invention with respect to five embodiments thereof it will be evident to those skilled in the art that many changes in the device could be made without departing from the spirit of the invention. Thus, the scope of the present invention should not be limited by the structures of the embodiments described in the specification, but only by the structures recited in the dependent claims and their equivalents.

We claim:

1. A device facilitating the inhalation of powdered medicaments from within capsules of the type each comprising a first capsule portion adapted to contain the powder and having an open end, and a second capsule portion closing the open end of the first capsule portion, said device comprising a body having walls defining a chamber in the upper portion thereof, a cavity adjacent the chamber, at least a portion of the cavity being located below the chamber, an air opening into said cavity for the entry of air, at least one inlet port up into said chamber from said lower portion of said cavity for the entry of air, and a mouthpiece having a central opening fluidically communicating with said chamber; a generally cylindrical support member having an axis and sockets extending radially and opening through its periphery adapted to receive and support the first capsule portions of a plurality of capsules, respectively, with the second capsule portions projecting from the sockets radially of the support member, said support member being mounted in the cavity of said body for rotation about said axis relative to said body, said inlet port being generally radially adjacent the support member, a portion of the periphery of the cylindrical support member adjacent said inlet port closing a portion thereof, means for moving said sockets one by one from a first position wherein a capsule received in the socket is outside said inlet port to a dispense position wherein the open end of the first capsule portion within the socket is within the confines of said inlet port between said air opening and mouthpiece so that airflow into said air opening and said inlet port and through said chamber induced by suction at the mouthpiece will cause the powdered medicament in the first capsule portion in the socket to become entrained in the airflow; and manually activatable means mounted on said body for removing the second capsule portion from the first capsule portion in the socket at said first position, said manually activatable means for removing comprising an extractor including means for frictionally engaging said second capsule portion, and manually actuatable means for moving the means for frictionally engaging relative to said body between a raised position at which raised position said means for frictionally engaging is spaced from the capsule in the socket of said support member at said first position, and an engage position at which engage position said means for frictionally engaging is in frictional engagement with the second capsule portion of the capsule within the socket of said support member at said first position.

2. A device according to claim 1 wherein the means for moving the sockets comprises coupling means engageable between said support member and said extractor for moving said sockets in said support member from said first position to said dispense position during movement of said extractor from said engage to said raised position.

3. A device according to claim 2 wherein said coupling means is a ratchet assembly, said ratchet assembly comprising a wheel having teeth about its periphery and attached to said support members, and pawl means coupled to said extractor for engaging and advancing said wheel during movement of said extractor from said engage position to said raised position.

4. A device according to claim 2 wherein said air opening is generally radially adjacent the support member and the manually actuatable means for moving the means for frictionally engaging relative to the body comprises means mounting said means for frictionally engaging on said body for radial movement with respect to said support member through said air opening between said engage and raised positions, bias means for biasing said means for frictionally engaging toward said raised position, and means for releasably latching said means for frictionally engaging in said engage position in opposition to said bias means, the means for releasably latching the means for frictionally engaging comprising a cover including a first portion adapted to cover the central opening in said mouthpiece and a second portion extending from the first portion and adapted to extend along said body over said means for frictionally engaging when said means for frictionally engaging is in said engage position, and means for pivotably mounting said cover on said body at the end of said second portion opposite said first portion for movement of said cover relative to said body between an open position with said first portion spaced from said mouthpiece and said second portion spaced from said body to allow movement of said means for frictionally engaging to said raised position under the influence of said bias means, and a closed position with said first portion of said cover over the central opening of said mouthpiece and said second portion of said cover retaining said means for frictionally engaging in said engage position, and wherein said second portion of said cover engages and moves said means for frictionally engaging from said raised position to said engage position upon movement of said cover from said open position to said closed position.

5. A device according to claim 2 wherein said air opening is generally radially adjacent the support member and the manually actuatable means for moving the means for frictionally engaging relative to the body comprises a cover including a first portion adapted to cover the central opening in said mouthpiece and a second portion extending from the first portion and adapted to extend along said body over said air opening, said second portion having formed thereon adjacent said air opening said means for frictionally engaging, and means for pivotably mounting said cover on said body at the end of said second portion opposite said first portion for movement of said cover relative to said body between an open position with said first portion spaced from said mouthpiece and said second portion spaced from said body and a closed position with said first portion of said cover over the central opening of said mouthpiece and said second portion of said cover over said air opening and wherein said second portion of said cover moves said means for frictionally engaging radially with respect to said support member, through said air opening, from said raised position to said engage position upon movement of said cover from said open position to said closed position.

6. A device according to claim 1 wherein said body includes means for directing airflow through said chamber substantially transversely across the open end of the first capsule portion in the socket in said support member at said dispense position.

7. A device according to claim 1 wherein said walls have a first upper surface that slopes downwardly relative to an imaginary plane substantially transverse across the open end of a socket in said support member at said dispense position, which first upper surface is between said air opening and said inlet port, and a second upper surface that slopes upwardly relative to said imaginary plane between said first surface and said inlet port with said upper surfaces having an intersection closely spaced from said support member to direct a portion of air flowing through said body into the first capsule portion in the socket at the dispense position.

* * * * *

UNITED STATES PATENT AND TRADEMARK OFFICE
CERTIFICATE OF CORRECTION

PATENT NO. : 4,860,740

DATED : August 29, 1989

INVENTOR(S) : Kirk et al.

It is certified that error appears in the above-identified patent and that said Letters Patent is hereby corrected as shown below:

Col. 8, line 2, after "the" second occurrence, insert --gripping walls 38--.

Col. 11, lines 8-9, delete "preceeding capsule 11 is opened and its first portions 12" and insert --first portion 12 of a preceding opened capsule 11--.

Signed and Sealed this

Sixth Day of November, 1990

Attest:

HARRY F. MANBECK, JR.

*Attesting Officer*  *Commissioner of Patents and Trademarks*